United States Patent [19]

Grinter

[11] Patent Number: 4,784,956

[45] Date of Patent: * Nov. 15, 1988

[54] VECTOR

[75] Inventor: Nigel J. Grinter, Caernarvon, Wales

[73] Assignee: Imperial Chemical Industries PLC, London, England

[*] Notice: The portion of the term of this patent subsequent to May 20, 2003 has been disclaimed.

[21] Appl. No.: 786,474

[22] Filed: Oct. 11, 1985

Related U.S. Application Data

[63] Continuation of Ser. No. 466,146, Feb. 14, 1983, Pat. No. 4,590,162.

[30] Foreign Application Priority Data

Feb. 17, 1982 [GB] United Kingdom ............... 8204573

[51] Int. Cl.$^4$ .................. C12N 15/00; C12N 1/20; C12N 1/00
[52] U.S. Cl. .............................. 435/172.3; 435/253; 435/320; 935/29; 935/52
[58] Field of Search ............... 435/172.3, 253, 317; 935/29, 52

[56] References Cited

U.S. PATENT DOCUMENTS 4,590,162  5/1986  Grinter ........................... 435/172.3

OTHER PUBLICATIONS

Barth et al, Journal of Bacteriology vol. 125, pp. 800–810 (1976).
Meyer et al, Molec. Gen. Genet. vol. 171, pp. 7–13 (1979).
Calos et al, Cell vol. 20, pp. 579–595 (Jul. 1980).
Gerard F. Barry; Bio/Technology vol. 4, May 1986; pp. 446–449; "Permanent Insertion of Foreign Genes into the Chromosomes of Soil Bacteria".
Nigel J. Grinter; Gene, 21 (1983) pp. 133–143 "A Broad–Host–Range Cloning Vector Transposable to Various Replicons".

Primary Examiner—Alvin E. Tanenholtz
Attorney, Agent, or Firm—Cushman, Darby & Cushman

[57] ABSTRACT

Novel transposable cloning vector and method of using it for the insertion into the chromosome of a recipient Gram-negative bacterium of DNA material foreign to that bacterium. The vector comprises first and second plasmids. The first plasmid carries a transposon (A) a part of whose DNA including the sequence which specifies its transposition function has been removed. The second plasmid carries a fragment of DNA from a transposon (A) including the sequence which specifies its transposition function. The DNA material to be inserted into the chromosome of the recipient bacterium is included in the DNA of transposon (A) carried by the first plasmid. Any suitable transposon may be used as transposon (A) but transposon Tn7 is preferred.

8 Claims, 3 Drawing Sheets

VECTOR

This is a continuation of application Ser. No. 466,146, filed Feb. 14, 1983, and now U.S. Pat. No. 4,590,162.

This invention relates to a transposable cloning vector having a broad host-range, to a method for inserting DNA using the vector, to novel microorganisms produced by the method and to novel plasmids used therein.

At the present time there is considerable interest in the developing techniques of genetic manipulation of microorganisms to produce new microorganisms having improved and useful properties. It is believed that such genetic manipulation techniques will become increasingly important industrially during the present decade. In such techniques it is usually necessary to take DNA material from one microorganism (or occasionally from some other source) and to transfer it into another microorganism. The vehicle used to transfer the DNA material is referred to as a vector. At the present time there exists a need for the development of broad host-range transposable vectors.

Recently a number of specialised vectors derived from bacterial plasmids and phages have been developed which allow the expression of cloned DNA fragments to be studied and controlled. These known vectors however have a limited host-range and lack complete stability and have been found not to be suitable for effecting permanent modifications in the biochemistry of potentially useful microorganisms. These modifications are best achieved by introducing the necessary genes (DNA material) into the chromosomes of recipient microorganisms.

Transposons are DNA sequences which are very useful in transferring genetic (DNA) material between plasmids, other particles and microorganisms. Transposons have the ability to move readily between different microorganisms, plasmids, etc., an ability which is coded for by a DNA sequence, contained within a transposon's overall sequence, termed the sequence specifying the transposition function in the transposon. Thus a plasmid containing a transposon in its DNA forms a useful vector for carrying a gene from one microorganism to another, the gene being introduced into the DNA of the transposon. However, the utility of such vectors has been limited because of a lack of stability, i.e. the mobility of the transposon means that it can be lost by or bring about deleterious genetic alterations in a recipient microorganism. Moreover previous use of transposons has not allowed selection for the introduction of genes into the chromosomes of recipient microorganisms.

According to the present invention we provide a vector for the transfer of DNA material between microorganisms which comprises a first plasmid and a second plasmid wherein the first plasmid carries a transposon (A), a part of whose DNA including the sequence which specifies its transposition function has been removed and the second plasmid carries a fragment of DNA from a transposon (A) including the sequence which specifies its transposition function, transposon (A) being any suitable transposon.

Further according to the present invention we provide a method for the insertion into the chromosome of a recipient Gram-negative bacterium of DNA material (B) foreign to that bacterium which comprises the steps of (1) constructing a vector-containing microorganism which contains a carrier plasmid and a helper plasmid, the carrier plasmid carrying any suitable transposon (A) into whose DNA has been included the foreign DNA material (B) to be inserted into the recipient bacterium and a part of whose DNA including the sequence specifying its transposition function has been removed and the helper plasmid carrying a fragment of DNA from a transposon (A) including the sequence specifying its transposition function, (2) transferring the carrier and the helper plasmids directly or indirectly from the vector-containing microorganism into the recipient bacterium and, (3) growing the recipient bacterium for sufficient generations and under suitable conditions for the inserted foreign DNA material (B) to pass into the chromosome of the recipient bacterium.

By the indirect transfer of the carrier and the helper plasmids from the vector-containing microorganism to the recipient bacterium we mean any mode of transfer containing a plurality of steps including transfers in which the plasmids pass from the vector-containing microorganism and into one or more intermediate microorganisms before passing into the recipient bacterium.

Suitably in or after step (3) of the method of the invention the carrier plasmid is lost from the recipent bacterium. Suitably after the inserted foreign DNA material (B) has passed into the chromosome of the recipient bacterium the helper plasmid is eliminated from the bacterium by the introduction thereinto of a plasmid incompatible with the helper plasmid (an incompatible plasmid).

Further according to the invention we provide novel Gram-negative bacteria into whose chromosomes foreign DNA material has been introduced by the vector and method of the invention, processes, including processes for the production of single cell protein, using such modified bacteria and novel plasmids and transposons for use in the vector or method and referred to in this specification. The novel plasmids of the invention include plasmids usable as first plasmids in the vector of the invention, second plasmids in the vector (i.e. corresponding to helper plasmids in the method) of the invention, carrier plasmids (i.e. first plasmids carrying transposons containing DNA material (B)) of the method of the invention and novel plasmids designed for use as incompatible plasmids (i.e. incompatible with helper plasmids). Specific plasmids to which the invention relates include carrier plasmid pNJ5073, modifications of this plasmid and first plasmids deriving from it or such a modification, second or helper plasmid pNJ9279 and modifications thereof and incompatible plasmid pGSS15 and modifications thereof.

In the remainder of this specification the invention will be described in terms of the method thereof. Effectively in the method of the invention the transposon used can be regarded as being divided into parts. One part containing the DNA sequence which specifies the transposition function of the transposon is located upon the helper plasmid whilst the other part, in which the sequence specifying the transposition function is replaced by the DNA material which is to be transferred using the method, is located on the carrier plasmid. Both the helper and the carrier plasmid are transferred into the recipient bacterium. Suitably the carrier plasmid is an unstable plasmid which is readily lost from the recipient bacterium. When the bacterium has been grown under suitable conditions for a number of generations (preferably at least 50 generations) the transferred foreign DNA material (B) passes into the chromosome of the recipient bacterium and if the carrier plasmid is unstable it is lost from the bacterium. At this stage a plasmid which is incompatable with the helper plasmid (the incompatible plasmid) can be introduced into the recipient bacterium to cause the helper plasmid also to be lost therefrom. It is of course to be understood that in the above description the two parts of the transposon are not necessarily or even probably from the same individual transposon sequence. The DNA containing the transposition function can be cut out of the total DNA sequence of the transposon by known means. Ideally only that sequence which specifies the transposition function is cut out and located upon the helper plasmid. However this is unlikely to be achieved so generally the transposon DNA carried by the helper plasmid will contain DNA additional to the sequence specifying the transposition function. This extraneous DNA is preferably kept to a minimum.

The method of the invention is very useful in instances where it is desired to transfer into a bacterium genetic material which modifies or adds to the general biochemical properties of the bacterium.

The carrier and helper plasmids are preferably transferred from the vector-containing microorganism (usually a bacterium) into the recipient bacterium in a single stage by conjugation. The carrier and helper plasmids are suitably plasmids having a broad host-range and the carrier plasmid at least is preferably an unstable plasmid which is readily lost from the recipient bacterium. Preferred carrier plasmids are derivatives of the promiscuous plasmid RP4 and preferred helper plasmids are derivatives of the plasmid R 300B. Other suitable carrier plasmids include R 751 and R 7K and other suitable helper plasmids include R 678 and PB165. Suitable incompatible plasmids include pGSS15 and Ap201. Plasmids used should have on them suitable markers, usually DNA sequences specifying resistance to particular antibiotics such as kanamycin resistance ($Km^R$), tetracycline resistance ($Tc^R$), trimethoprim resistance ($Tp^R$) and streptomycin resistance ($Sm^R$) so that their presence or absence in bacterial cells may be determined.

The method of the invention can be used to effect a wide range of useful genetic manipulations. Examples of manipulations which can be performed include the introduction of genetic information into the chromosome of a bacterium which allows it to utilize novel energy sources or to improve the efficiency of its energy conversion. Examples of bacteria which may be used either as the vector containing microorganism or as the recipient bacterium include strains of *E. coli* and of *Methylophilus methylotrophus* (formerly named *Pseudomonas methylotropha*). The species *Pseudomonas methylotropha* is described in our UK Patent Specification No. 1370892 which also describes a number of specific strains of this species i.e. strains NCIB Nos. 10508-15 and 10592-96. In our Examples we describe that use of the method of the invention in *E. coli* and *Methylophilus methylotrophus*. Cultures of the modified strains have been deposited at the National Collection of Industrial Bacteria (NCIB, Torrey Research Station, Aberdeen, Scotland, UK) and have been given the deposition numbers NCIB 11714 and NCIB 11715 (modified *E. coli* strains).

Most of the transposons may be used in the method of the invention for instance any of Tn1 to Tn7 (we are not aware of a transposon Tn8 or Tn10). However transposon Tn7 is preferred. Any DNA fragment generated by the restriction enzymes HindIII or BamHI can be inserted directly into the DNA of Tn7, e.g. on plasmid pNJ5070 described in Example 2 and FIG. 1.

The invention is illustrated by the accompanying drawings wherein.

Figure 1:
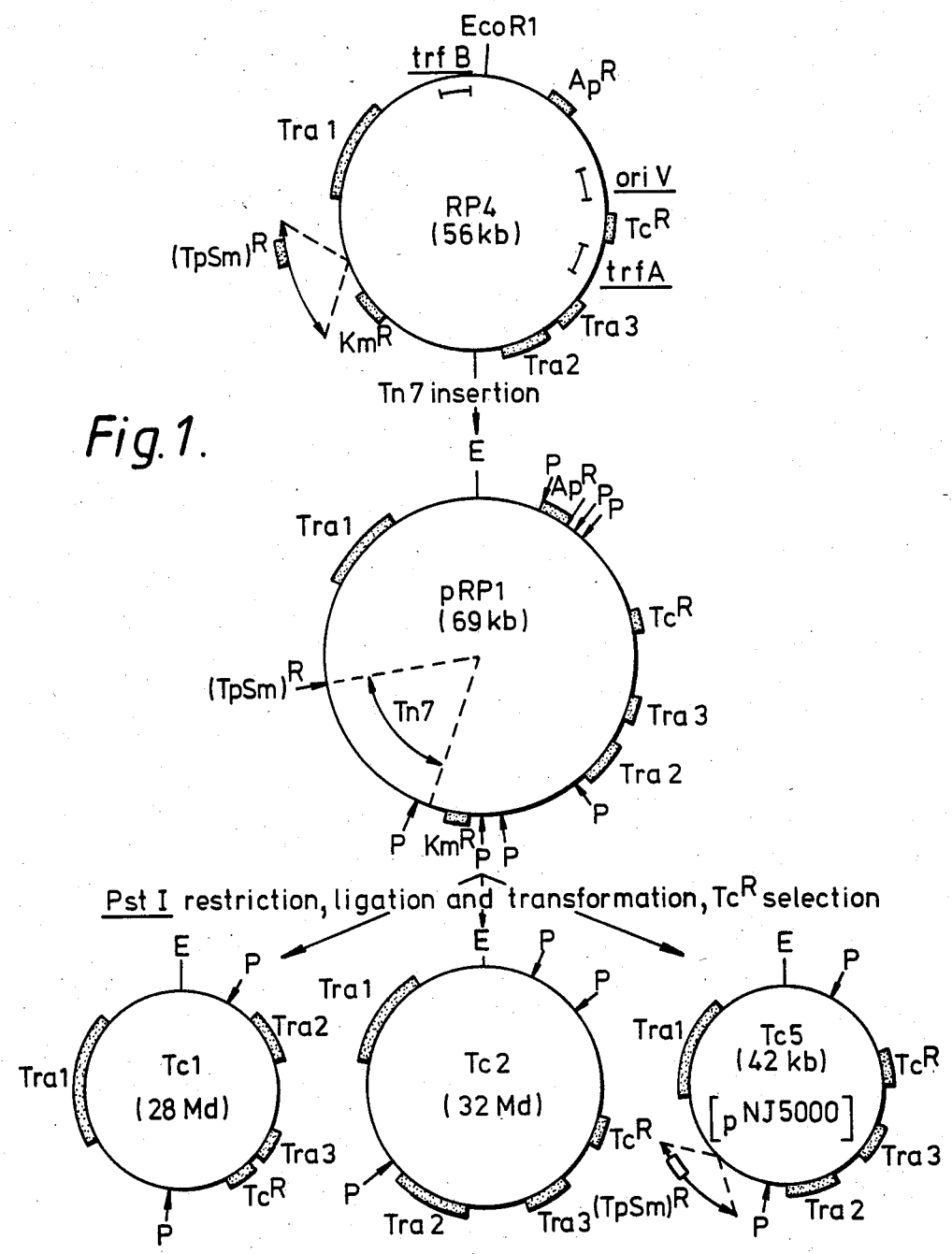
FIG. 1 is a diagram showing the derivation of plasmid pNJ5000 from plasmid RP4.
Figure 2:
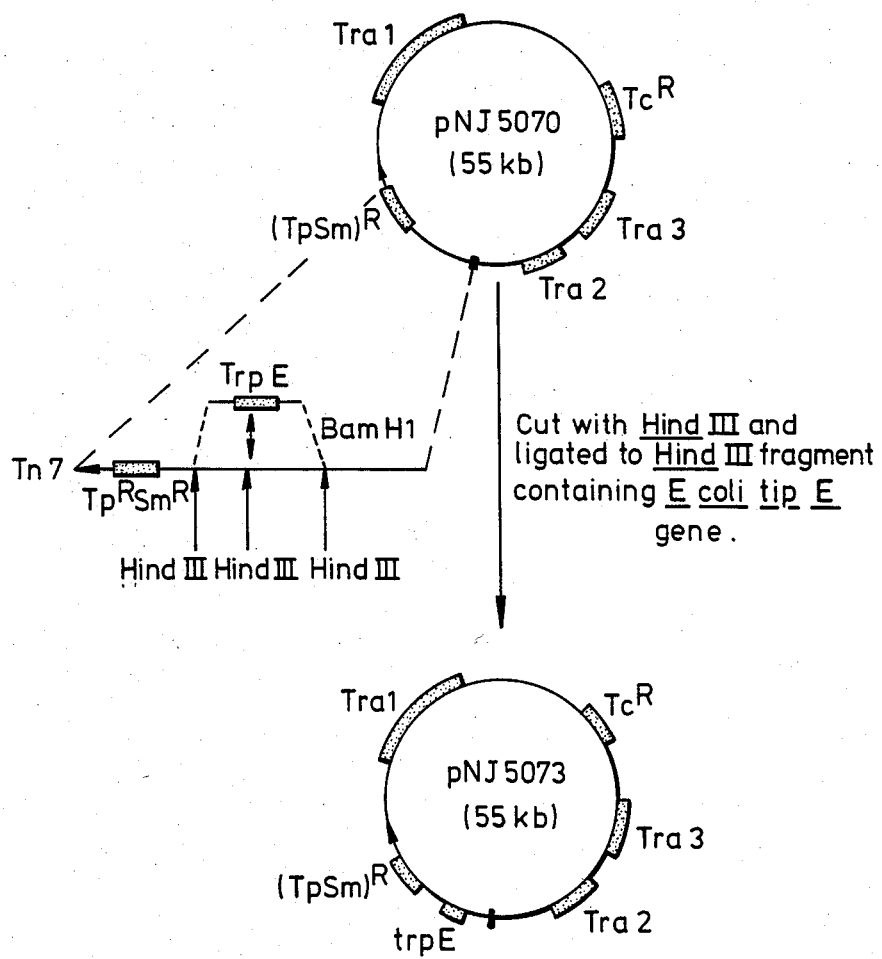
FIG. 2 is a diagram showing the derivation of plasmid pNJ5073 from plasmid pNJ5070.
Figure 3:
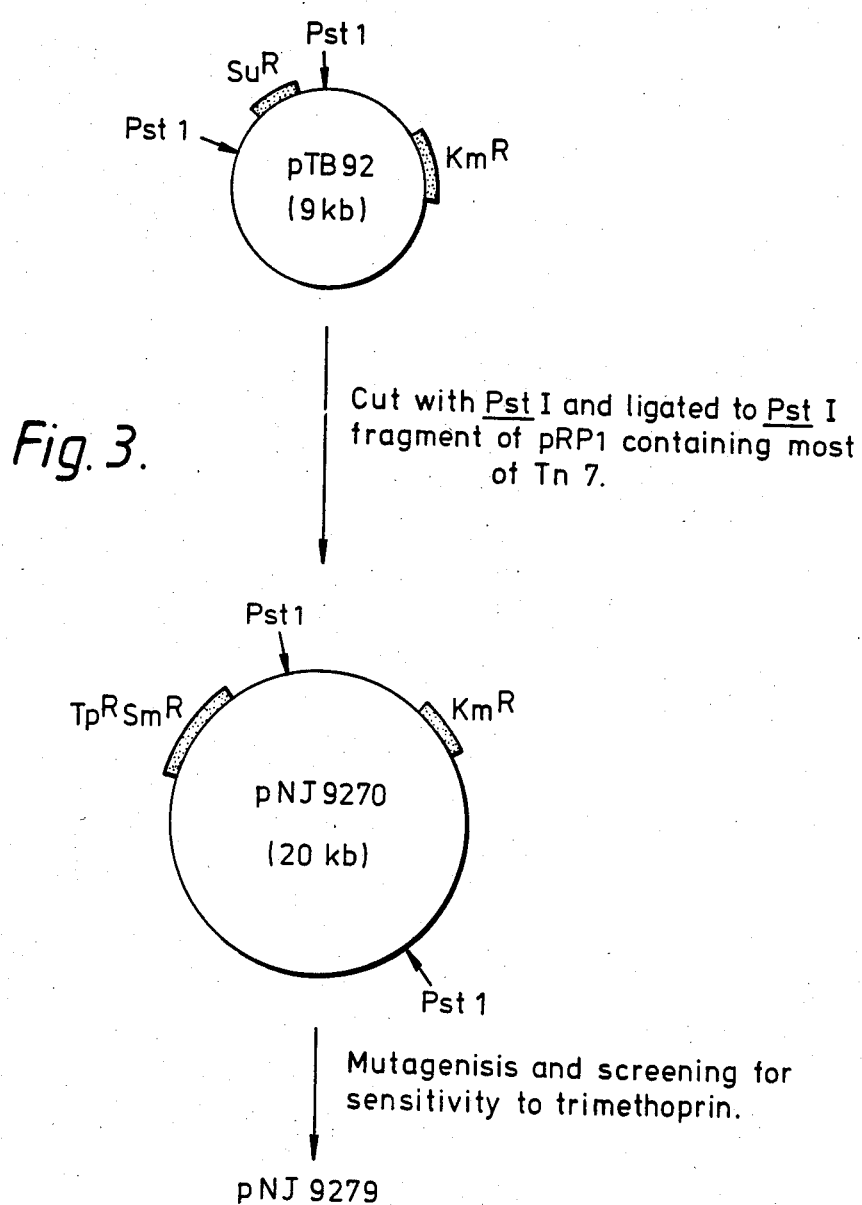
FIG. 3 is a diagram showing the derivation of plasmid pNJ9279 from plasmid pTB92.

Together FIGS. 1 and 2 show the derivation of the carrier plasmid pNJ5073 which is described hereinafter at section (a) of Example 1. FIG. 3 shows the derivation of helper plasmid pNJ9279 which is described hereinafter in Section (b) of Example 1.

The invention is illustrated by the following Examples wherein Example 1 describes the derivation of a carrier plasmid pNJ5073 and a helper plasmid pNJ9279 (the component plasmids of the vector) and Examples 2 and 3 show the use of the vector in *E.coli* and *Methylophilus methylotrophus* respectively.

EXAMPLE 1

Derivation of plasmids used in transposable vector system (a) Plasmid pNJ5073

The starting point is plasmid RP4, a naturally occurring plasmid belonging to incompatibility group P (IncP) and coding for resistance to the antibiotics Ampicillin (Ap), Tetracycline (Tc) and Kanamycin (Km). It also carries genes determining the ability to transfer itself by conjugation into a very wide range of Gram-negative bacteria. Its molecular size is approximately 56 kilobases (kb) and the arrangement of genes on the DNA molecule is as shown in FIG. 1. This shows the location of the regions (Tra1, 2 and 3) involved in conjugal transfer and also the location of the functions essential for the replication and maintenance of the plasmid within its bacterial host (trfA, trfB and oriV).

The next stage is the insertion of the 13kb DNA sequence Transposon 7 (Tn7) at the site shown to give the derivative pRP1. Tn7 carries genes coding for resistance to the antibiotics Trimethoprim (Tp) and Streptomycin (Sm), as well as genes conferring the ability of this 13kb DNA sequence to transpose itself from one DNA molecule to another. A map of pRP1 is also shown in FIG. 1. The eight sites marked with the letter P around the pRP1 DNA molecule denote the points at which the restriction enzyme PstI cleaves the plasmid molecule. After PstI cutting in vitro, the fragments of pRP1 were annealed in various combinations using the enzyme DNA ligase and then reintroduced into the bacterium *Escherichia coli* K12 by transformation. One of the novel plasmid types obtained in this way (Tc5 or pNJ5000) was used for the next stage.

pNJ5000 has lost the genes present on pRP1 which determine $Ap^R$, $Km^R$, $Tp^R$ and $Sm^R$, but retains $Tc^R$ and all the genes concerned with replication, maintenance and transfer by conjugation. It has also become highly unstable, being lost by approximately 5% of the cell population per generation if it is not selected by the presence of tetracycline in the growth medium. Transposon 7 is now re-inserted as shown to generate plasmid pNJ5070.

The DNA sequences deleted from pRP1 in the formation of pNJ5000 contain all the sites on that plasmid which are recognised by the restriction enzymes HindIII and BamHI. Therefore, when Tn7 is inserted into pNJ5000 to generate pNJ5070 the only HindIII and BamHI sites on pNJ5070 are those within Tn7 (see FIG. 2).

pNJ5070 DNA was cut with HindIII, whereby removing a large central section of Tn7, and then joined with HindIII-generated DNA fragment containing the trpE gene of Escherichia coli K12 to generate pNJ5073 as shown in FIG. 2.

(b) Plasmid pNJ9279

This was derived from plasmid pTB92, which is itself a derivative of R300B, a naturally occurring broad host-range plasmid. pTB92 belongs to incompatibility group Q (InCQ) and confers resistance to the antibiotics Sulphonamide (Su) and Kanamycin (Km). It does not encode functions for transfer by conjugation, but is readily transferred (mobilised) if another plasmid which does determine a conjugation system (e.g. RP4) is present in the same bacterial cell.

pTB92 contains two DNA sequences which are recognized by the restrictions enzyme PstI (see FIG. 3). These sequences are on either side of the gene specifying Su resistance. pTB92 DNA was cut with PstI, thereby excising the Su resistance gene, and joined by DNA ligase with the PstI fragment of pRPI which contains most of Tn7. This fragment includes the antibiotic resistance genes and the region deleted from pNJ5073; it is incapable of transposition, however, because it lacks DNA sequences from one end of the transposon. The resultant plasmid, pNJ9270, was reintroduced into *Escherichia coli* K12 by transformation.

As a final step, a mutant was selected which no longer confers resistance to Tp. This was designated pNJ9279.

EXAMPLE 2

Use of the transposable vector system in *E. coli*

All of these experiments was carried out in a bacterial strain which cannot grow in the absence of the amino acid tryptophan because of a mutation in the trpE gene. All stages, except where stated, were carried out in the presence of tryptophan.

Plasmids pTB92 and pNJ9279 were introduced by transformation with selection for kanamycin resistance (Km$^r$); pNJ5070 and pNJ5073 were transferred by conjugation, selecting for tetracycline resistance (Tc$^R$), and the following plasmid combinations were established:
1. pNJ5070
2. pNJ5073
3. pNJ5073+pTB92
4. pNJ5073+pNJ9279

Representatives of each plasmid combination were tested for their ability to grow without tryptophan. Only bacteria harbouring pNJ5073 (which carries the trpE gene inserted into Tn7) were able to grow without it.

Examples of bacteria carrying each plasmid combination were then grown in medium containing tryptophan and Tp (to select for Tn7); Km was also added if pTB92 or pNJ9279 were present. Cultures were then maintained in this medium for a period of approximately fifty generations of bacterial growth. This period allows the unstable plasmid (pNJ5070 or pNJ5073) to be lost providing it can first donate a copy of Tn7 to the bacterial chromosome. Following this loss, the bacterium becomes sensitive to Tc.

Thirty separate isolates from each of the four plasmids combinations were therefore tested for sensitivity to Tc, Tp$^R$ and ability to grow without tryptophan, with the following results:
1. 30/30 Tc$^S$Tp$^R$ tryptophan dependent (Trp$^-$)
2. 30/30 Tc$^R$Tp$^R$ tryptophan independent (Trp+)
3. 30/30 Tc$^R$Tp$^R$Trp+
4. 16/30 Tc$^S$Tp$^R$Trp+, 8/30 Tc$^R$Tp$^R$Trp+, 6/30 Tc$^S$Rp$^R$Trp$^-$ The results demonstrate that pNJ5070, which carries a normal Tn7, can donate the transposon and then be lost from the bacterial host; pNJ5073, however, which carries a Tn7 which has sustained a deletion of DNA from the central region, cannot donate the transposon and therefore the plasmid is retained by the bacterium. Further, the presence of pTB92 has no effect on this. If, however, as in No. 4, pNJ9279 carrying the central region of Tn7 is present, then about one half of the isolates tested have characteristics consistent with their having undergone transposition. This was confirmed by taking two Tc$^S$Tp$^R$Trp+isolates from No. 4 and transforming them with the DNA of plasmid pGSS15 selecting for ampicillin resistance (Ap$^R$). pGSS15 is a plasmid of the same incompatibility group as pNJ9279 (InCQ) and consequently its introduction leads to the loss of pNJ9279, as indicated by the bacteria becoming sensitive to Km. In both cases, however, the bacteria containing pGSS15 remained Tp$^R$ and could still grow without tryptophan, demonstrating that transposition of Tn7 with the cloned trpE gene had taken place to the bacterial chromosome.

To show that the chromosomal insertion of Tn7+trpE is stable, RP4 was introduced by conjugation into an isolate containing it, and also into an isolate containing a normal Tn7 in the chromosome. Both RP4 containing strains were then used as conjugal donors to a distinguishable *E. coli*, with selection for transfer of either RP4 (Tc$^R$) or Tn7 (Tp$^R$). If the donor contained a normal Tn7, then roughly 5 in 10,000 of the bacteria which received RP4 also inherited Tn7 which was transferred by transporting to RP4 and then being transferred during conjugation. If the donor contained a defective Tn7 with an inserted trpE gene, however, then no transfer of Tp$^R$ was detected (i.e. it was at least 1000 times less efficient). This shows that the disabled Tn7 is a stable part of the chromosome.

EXAMPLE 3

Use of the transposable vector system in *Methyophilus methylotrophus* Strain NCIB 10515

An *E. coli* strain containing both pNJ5073 and pNJ9279 was used to transfer both plasmids to *M. methylotrophus* by conjugation, with selection for Tc$^R$ and Km$^R$. Isolates of the doubly resistant *M. methylotrophus* were grown for approximately 50 generations with Tp and Km selection. At the end of this period, ten isolates from each were tested for their antibiotic resistance patterns. All were Tc$^S$Tp$^R$Km$^R$ i.e. they had characteristics consistent with their having undergone transposition. To confirm that transposition to the chromosome had occurred, pGSS15 was introduced into three Tc$^S$Tp$^R$Km$^R$ isolates by mobilisation with pNJ5055, another unstable RP4 derivative. pNJ9279 was eliminated as indicated by Km$^S$, but Tp$^R$ was retained in all three cases. This confirms that transposition to the *M.* methylotrophus chromosome had taken place. Further, the insertion was shown to be stable by growth through approximately 50 generations without Tp selection followed by testing for loss of $Tp^R$. No loss was detected in 100/100 isolates tested.

Plasmids pNJ5073 and pNJ9279 in strains of E. coli have been deposited at the National Collection of Industrial Bacteria (NCIB), Torrey Research Station, Aberdeen, Scotland, UK and the strains have been given the accession numbers NCIB 11714 and 11715 respectively.

The plasmid prefix designation pNJ has been registered at the Plasmid Reference Centre maintained by Esther M. Lederberg at the Department of Medical Microbiology, Stanford University, Stanford, Conn., USA.

I claim:

1. A vector for the transfer of DNA material between microorganisms which comprises a first plasmid and a second plasmid wherein the first plasmid carries a transposon (A), a part of whose DNA including the sequence which specifies its transposition function has been removed and the second plasmid carries a fragment of DNA from a transposon (A) including the sequence which specifies its transposition function, transposon (A) being any suitable transposon.

2. A method for the insertion into the chromosome of a recipient Gram-negative bacterium of DNA material (B) foreign to that bacterium which comprises the steps of (1) constructing a vector-containing microorganism which contains a carrier plasmid and a helper plasmid, the carrier plasmid carrying any suitable transposon (A) into whose DNA has been included the foreign DNA material (B) to be inserted into the recipient bacterium and a part of whose DNA including the sequence specifying its transposition function has been removed and the helper plasmid carrying a fragment of DNA from a transposon (A) including the sequence specifying its transposition function, (2) transferring the carrier and the helper plasmids directly or indirectly from the vector-containing microorganism into the recipient bacterium and, (3) growing the recipient bacterium for sufficient generations and under suitable conditions for the inserted foreign DNA material (B) to pass into the chromosome of the recipient bacterium.

3. A method according to claim 2 wherein the carrier plasmid is lost from the recipient bacterium in or after step (3) of the method.

4. A method according to claim 2 wherein after the inserted foreign DNA material (B) has passed into the chromosome of the recipient bacterium the helper plasmid is eliminated from the bacterium by the introduction thereinto of a plasmid incompatible with the helper plasmid (an incompatible plasmid).

5. A method according to claim 2 wherein the carrier plasmid is selected from the group consisting of plasmids R751, R7K and derivatives of plasmid RP4.

6. A method according to claim 2 wherein the helper plasmid is selected from the group consisting of plasmids R678, PB165 and derivatives of plasmid R300 B.

7. A method according to claim 2 wherein the vector-containing microorganism and the recipient bacterium are selected from the group consisting of strains of the species E. coli and Methylophilus methylotrophus.

8. A method according to claim 2 wherein the transposon (A) is transposon Tn 7.

* * * * *